United States Patent [19]

Muldoon

[11] 4,024,872
[45] May 24, 1977

[54] COLOSTOMY DEVICE AND METHOD

[76] Inventor: James P. Muldoon, 1942 Sherman, SE., East Grand Rapids, Mich. 49506

[22] Filed: June 1, 1976

[21] Appl. No.: 691,346

[52] U.S. Cl. .............................................. 128/348
[51] Int. Cl.² ...................................... A61M 25/00
[58] Field of Search ............... 128/132 R, 1 R, 248, 128/303 R, 283, 287, DIG. 24, 348

[56] References Cited

UNITED STATES PATENTS

| | | | |
|---|---|---|---|
| 3,674,032 | 7/1972 | Minganti | 128/132 R |
| 3,709,220 | 1/1973 | Boyden | 128/132 R |
| 3,854,477 | 12/1974 | Smith | 128/348 |
| 3,906,951 | 9/1975 | Ling | 128/283 |

*Primary Examiner*—Lawrence W. Trapp
*Attorney, Agent, or Firm*—Price, Heneveld, Huizenga & Cooper

[57] ABSTRACT

A surgical method and device for performing colostomy or like surgery in which a sterile, flexible plastic sleeve is slipped over the bowel or colostomy spur and lubricated. The sleeve covered spur is then pulled through the relatively small colostomy incision until the colostomy spur has protruded to the satisfaction of the surgeon. Then the sleeve is pulled completely out of the incision and off of the spur. The sleeve itself is notched at one end to facilitate clamping and tying by means of at least one suture fastened to the sleeve above the base of the notch.

16 Claims, 6 Drawing Figures

COLOSTOMY DEVICE AND METHOD

BACKGROUND OF THE INVENTION

The present invention relates to colostomy or like surgery in which a portion of the bowel, referred to as the colostomy spur, must be pulled through a small opening or incision in the abdominal wall. FIG. 1 of the drawings illustrates the basic prior art procedure. First, a large incision (7-10 inches) is made in the abdominal wall 21 to open the abdominal cavity 20. The bowel transection is then completed. The rectum 40 is capped by means of a cover 41 as is conventional. the colostomy spur 60 is then pulled through a relatively small colostomy incision 50 which has been made in the abdominal wall off to one side, away from the major incision. Once spur 60 has been pulled through, by means of a clamp 70 or the like, it is either left in situ or it is matured, depending on whether the colostomy is temporary or permanent.

One problem encountered in a colostomy is that the tissue on the surface of the colostomy spur 60 does not slide well against the fatty tissue defining the perimeter of the relatively small colostomy incision in the abdominal wall. The colostomy incision cannot be made too large or the patient suffers from paracolostomy herniation. Because the incision must be small, the surface of the colostomy spur is in intimate contact with the surface of the incision perimeter as the spur is pulled through the perimeter.

This creates a tissue traumatic situation which can result in postoperative internal bleeding and even in devitalization of the spur. These conditions require repetition of the operation and such repetition is considered a significant disaster by surgeons who perform this operation.

Accordingly, surgeons must delicately balance the problems encountered in making the colostomy incision too large on the one hand versus those of making the incision too small on the other. Surgeons have been living with these problems for many years and have relied on their experience to help them effectuate the required balance.

SUMMARY OF THE INVENTION

In the present invention, the surgeon eliminates the above problems by using a surgical method and device in which a flexible, sterile plastic sleeve is slipped over the end of the transected colostomy spur so that it extends from approximately the end of said spur a distance along the length thereof sufficient to allow the sleeve covered spur to be pulled through the relatively small colostomy incision with only said sleeve making contact with the perimeter of the incision. The sleeve is lubricated and the lubricated sleeve covered spur is then drawn through the relatively small incision such that the surface of the spur itself never comes into contact with the surface of the incision perimeter. When the spur has been pulled through the incision a distance satisfactory to the surgeon, the surgeon slides the sleeve the rest of the way through the incision and off over the end of the colostomy spur.

Preferably, the sleeve itself includes a notch extending from one end thereof to facilitate clamping the end of the colostomy spur closed with a clamp while simultaneously tying off the end by means of at least one suture affixed to the end of the sleeve above the base of the notch and above the level of the clamp. The sealing clamp can then be removed just before delivery of the spur through the relatively small incision in the abdominal wall.

As a result of the present invention, tissue trauma heretofore encountered during the drawing step is minimized and sterility of the procedure is increased by the presence of the sterile sleeve. These and other objects, advantages and features of the invention will be more fully understood and appreciated by reference to the written specification and appended drawings.

DESCRIPTION OF THE PREFERRED EMBODIMENT

In the preferred embodiment, the colostomy sleeve 10 of the present invention comprises a flexible, sterile plastic sleeve 10. The plastic employed must be flexible and must be sufficiently durable that it does not tear as the sleeve covered spur is being pulled through the colostomy incision. Also, the plastic must be a material which can be sterilized without deterioration. Finally, the plastic 10 should be transparent (at least after sterilization and prior to use) so that a surgeon can observe and assess the viability of the spur during all stages of the operation. I have found that nylon film of a thickness of approximately 1 mil is satisfactory. Portex Division of Smith Industries, Inc., Gill Street, Woburn, Massachusetts offers such a film on a roll, in sleeve form, for use in packaging sterilized instruments. They designate it as size 5, type B.

Figure 2:
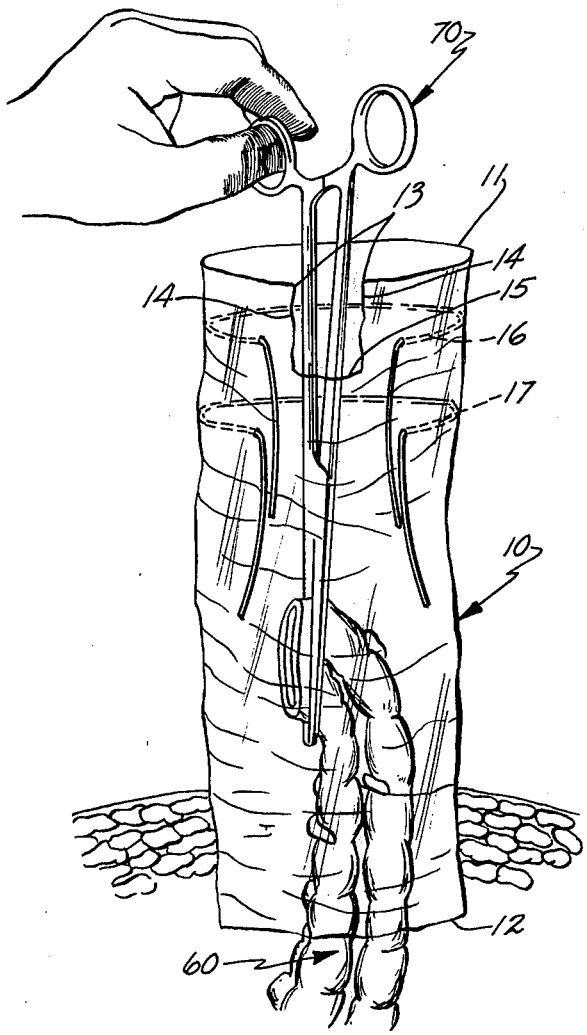
FIG. 2 is an elevational view of the colostomy sleeve of the present invention being slipped over the end of the colostomy spur, and over the sealing clamp which is being used to seal that end.

Sleeve 10 must be sufficiently large in diameter that it can readily be slipped over a clamp 70 being used to hold the end of spur 60 closed and over the spur itself with as little difficulty as possible (FIG. 2). It must be sufficiently long that when the spur 60 is pulled through the incision to the degree desired by the surgeon, only the surface of the flexible sleeve 10 itself has come into contact with the surface of the perimeter of the colostomy incision 50. I have found approximately 12 inches to be a satisfactory length and about 2 inches when opened to a circular cross section to be a satisfactory diameter. Since spurs vary in length, the sleeve can be tailored during the operation. The 12 inch length insures sufficient length.

Figure 1:
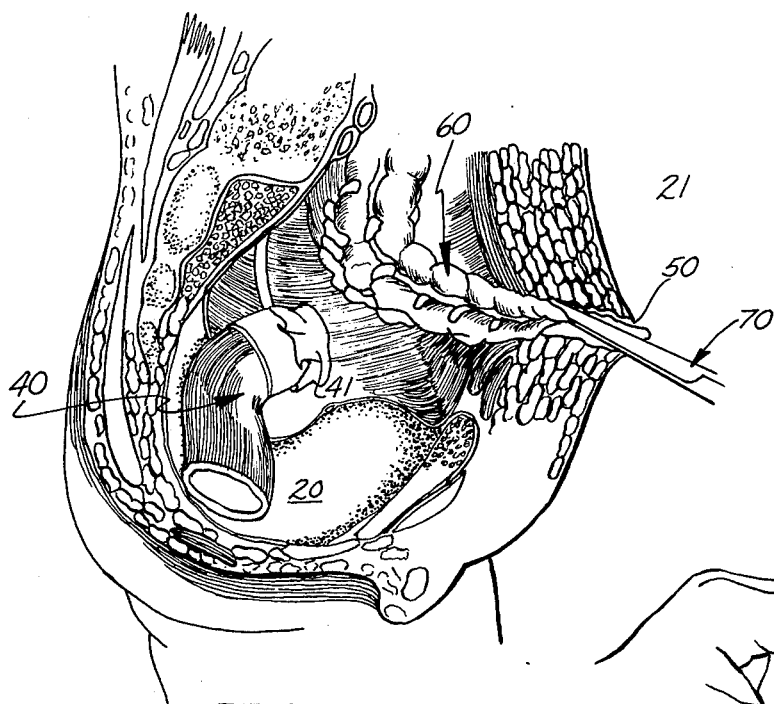
FIG. 1 is a cross-sectional view of the abdominal cavity of the human body, taken on a plane through the small colostomy incision, with a colostomy being performed in accordance with prior art techniques.
Figure 3:
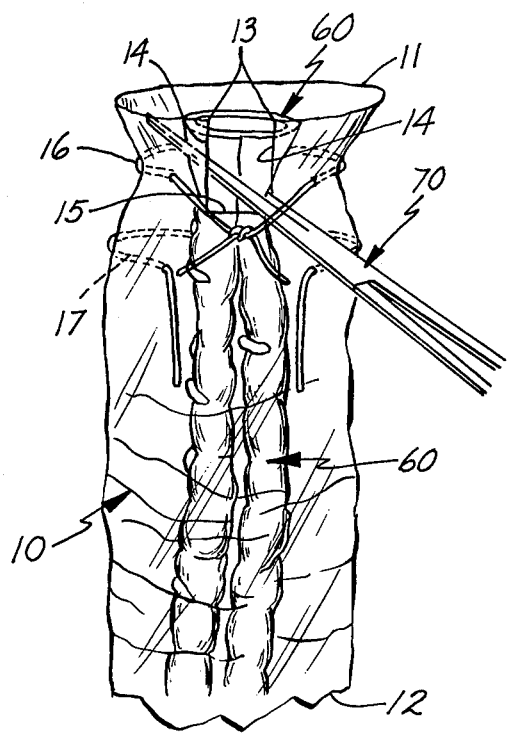
FIG. 3 is an elevational viewing showing the clamp extending out through the notch in the end of the sleeve with the suture being tied above the level of the clamp.

Preferably, flexible plastic sleeve 10 includes a notch 13 which extends from one end 11 of flexible sleeve 10 away therefrom a distance of about 1½ inches to a base edge 15. The 1½ inches are sufficiently long to allow one to, in essence, lay clamp 70 in notch 13 and tie a suture 16 around sleeve 10 and around the end of colostomy spur 60 at a point above the level of clamp 70 (FIG. 3). The width of notch 13 between its side edges 14 is sufficiently large to allow clamp 70 to lie therebetween.

Suture or tie 16 which is tied above clamp 70 is referred to as proximate suture 16 since it is closest to the notched end 11 of sleeve 10. It is sewn to sleeve 10 about its circumference in a conventional manner and at a point so that when tied, it is located above the base edge 15 of notch 13 a distance which is sufficient to allow clamp 70 to lie between base edge 15 and proximate suture 16.

A second suture or tie, referred to as a distal suture 17, is located on sleeve 10 at a point spaced from proximate suture 16 in a direction away from notch end 11. Distal suture 17 is also sewn onto sleeve 10 and is spaced from proximate suture 16 a distance which is large enough to allow clamp 70 to lie between the two sutures. Distal suture 17 does not need to overlie notch 13 and in fact preferably is located below the base edge 15 of notch 13 toward the opposite end 12 of sleeve 10. Distal suture 17 is necessary to insure that sleeve 10 does not slide off spur 60 during handling and therefore should be located farther from the end 11 of sleeve 10.

The term suture as used herein is not intended to be limited to any specific type of material. It is only important that the material be durable and sterilizable. In essence, the sutures or ties serve a clamping function.

The operational procedure begins the same as is conventional for colostomy. A large incision is made in the abdominal wall 21 so as to expose the interior of the abdominal cavity 20. The transection is performed and the rectum is sealed as is conventional.

The transected colostomy spur is sealed at its end by means of a sealing clamp 70 (FIG. 2). the surgeon slides sterile, flexible plastic sleeve 10 over clamp 70 and down over colostomy spur 60 (FIG. 2).

When the end of spur 60 comes approximately to the end 11 of flexible sleeve 10, clamp 70 is turned so that it extends laterally from spur 60 and from sleeve 10. Clamp 70 is also located so that it lies within notch 13 (FIG. 3). Proximate suture 16 is tied above clamp 70 and distal suture 17 is tied below clamp 70. Clamp 70 can then be removed and is removed just prior to delivery of the sleeve covered spur 60 to the small colostomy incision 50. Once sleeve 10 is in place on spur 60, it is lubricated by the surgeon, preferably simply employing fluids which are available within the abdominal cavity 20.

Figure 4:
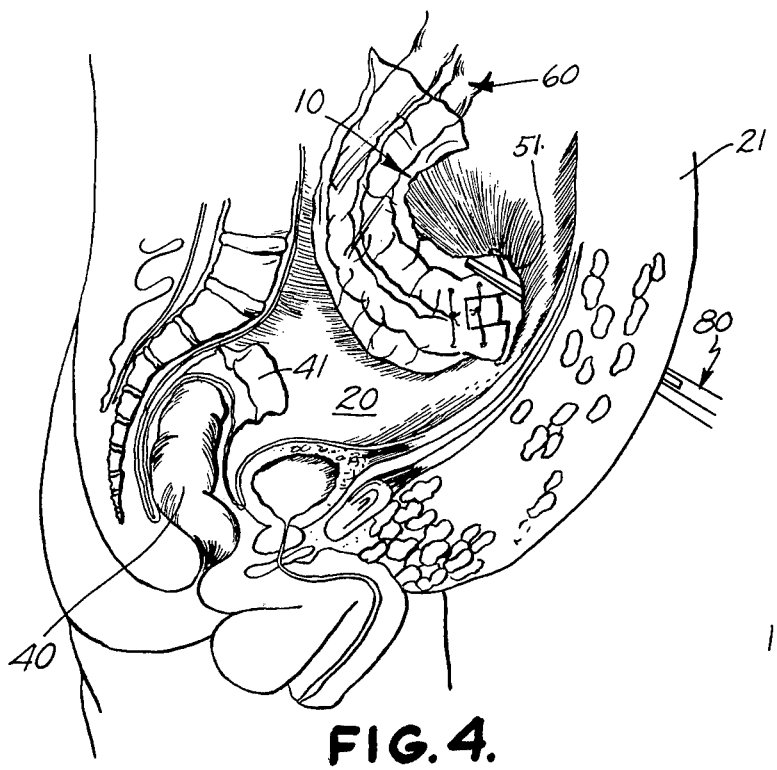
FIG. 4 is a cross-sectional view of the abdominal cavity taken on a plane through the large, main incision with the sleeve enclosed colostomy spur in a condition such that it is about to be drawn through the relatively small colostomy incision.
Figure 5:
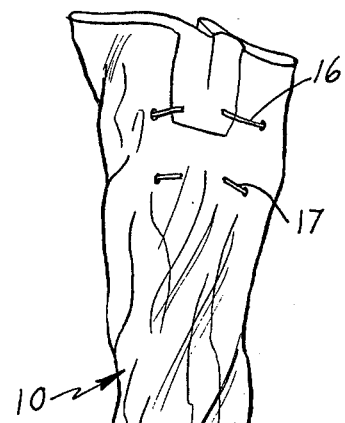
FIG. 5 is a cross-sectional view of the abdominal wall at the small colostomy incision showing the sleeved colostomy spur after it has been drawn through the incision.
Figure 5:
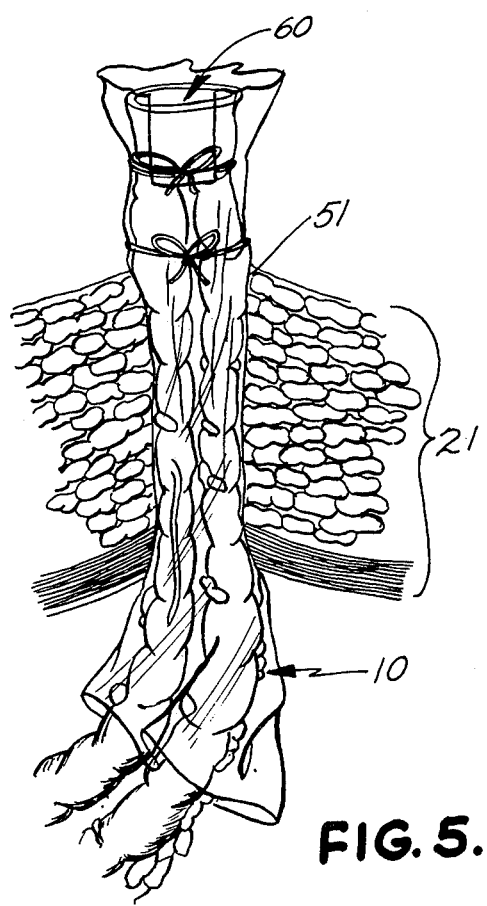

Then colostomy incision 50, a relatively small incision, is made in the abdominal wall 21 at a point spaced from the main incision. Another clamp 80 is inserted through colostomy incision 51 and is used to grasp the sleeve covered end of colostomy spur 60 (FIG. 4). The sleeve covered spur 60 is drawn through incision 51 until it protrudes from incision 51 a distance satisfactory to the surgeon (FIG. 5). Usually this is about 2 or 3 inches.

Figure 6:
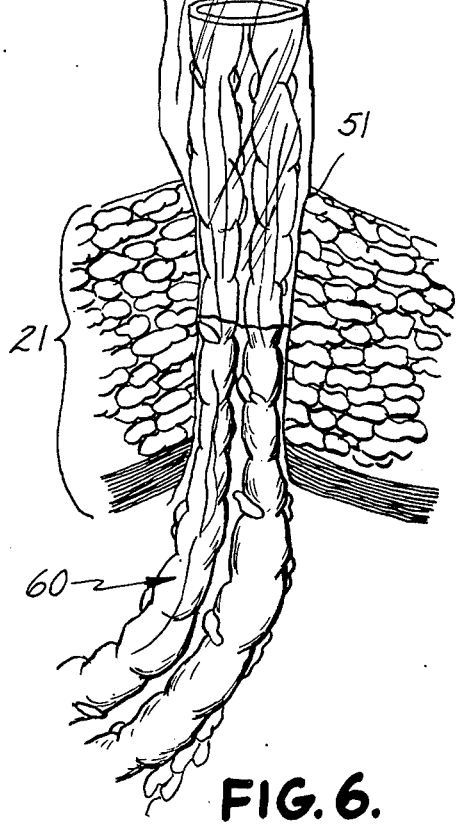
FIG. 6 is the same cross-sectional view as FIG. 5 showing the colostomy sleeve after the sutures have been snipped, and as the sleeve is being pulled completely through the colostomy incision and off the end of the colostomy spur.

The surgeon then snips the tied sutures 16 and 17 and slides flexible sleeve 10 upwardly through colostomy incision 51 and completely off the end of colostomy spur 60 (FIG. 6). This leaves the surface of spur 60 in intimate contact with the tissue defining the perimeter of incision 51. Since spur 60 does not have to be moved any further, there will be no trauma as a result of this contact. The operation is then completed in a conventional manner, with the spur 60 either being left in situ or matured, depending on whether or not the operation is to be a temporary or permanent colostomy.

Because flexible plastic sleeve 10 slides readily against the perimeter of incision 51, traumatic damage to both the surface of the perimeter of incision 51 and the surface of colostomy spur 60 is greatly reduced, if not almost entirely eliminated. Problems of devitalization are substantially eliminated. Further, the sleeve of the present invention enhances sterility of the operation by creating a colostomy tie-off to prevent spillage with resulting contamination of the abdominal cavity 20. Of course, it will be understood that the above is merely a preferred embodiment of the invention and that various changes and alterations can be made without departing from the spirit and broader aspects of the invention.

The embodiments of the invention in which an exclusive property or privilege is claimed are defined as follows:

1. A method for drawing a colostomy spur or like body organ through a body incision which is sufficiently small relative to said spur that intimate contact between the surface of said spur and the perimeter of said incision would normally occur during the normal drawing operation, said method eliminating said contact and comprising: slipping a flexible, sterile plastic sleeve over the end of the transected colostomy spur so that said sleeve extends from approximately the end of said spur a distance along the length thereof sufficient to allow the sleeve covered spur to be pulled through the relatively small, body incision with only said sleeve making contact with the perimeter of said incision; drawing said sleeve and sleeve covered colostomy spur through said relatively small incision whereby traumatic contact between said perimeter of said incision and said colostomy spur is eliminated; removing said sleeve by sliding said sleeve completely through said incision and off said spur over the end thereof.

2. The method of claim 1 which comprises: employing as said sleeve a flexible, sterile plastic sleeve having a notch extending from one end thereof to a notch base a distance which is sufficient to allow one to clamp the end of said spur and orient said clamp such that it extends laterally from said spur and from said sleeve and lies within said notch, said sleeve further including at least one tie fixed in the vicinity of said one end for tying around the circumference of said sleeve and around said spur, said tie being located at a point spaced from said base of said notch toward said one end of said sleeve such that when said tie is tied, it will be tied above the level of said clamp.

3. The method of claim 2 in which said step of employing said flexible plastic sleeve includes employing a sleeve having a second tie spaced from said first tie in a direction away from said one end a distance sufficient to allow said clamp to lie between said first and second ties when they are tied.

4. The method of claim 3 in which said step of employing said flexible plastic sleeve includes locating said second tie below said base of said notch.

5. The method of claim 4 in which said step of employing said flexible plastic sleeve comprises: employing a flexible plastic sleeve of a transparent, plastic material so that the surgeon can observe and assess the viability of the spur as the operation is proceeding.

6. The method of claim 5 in which said step of employing said plastic sleeve comprises employing a sleeve made of a nylon film material.

7. The method of claim 1 in which said step of employing said flexible plastic sleeve comprises: employing a flexible plastic sleeve of a transparent, plastic material so that the surgeon can observe and assess the viability of the spur as the operation is proceeding.

8. The method of claim 1 in which said step of employing said plastic sleeve comprises employing a sleeve made of a nylon film material.

9. The method of claim 1 in which the surface of said sleeve is lubricated prior to drawing said sleeve covered spur through said incision.

10. A surgical device for use in colostomy surgery or the like in which a colostomy spur or like body organ is drawn through a body incision which is sufficiently small relative to said spur that intimate contact between the surface of said spur and the perimeter of said incision will normally occur during performance of the operation in accordance with normal procedures, said surgical device eliminating such contact and comprising: a flexible, sterilizable plastic sleeve of sufficient length that said sleeve can be slipped over the end of a transected colostomy spur so as to extend from approximately the end of said spur a distance along the length thereof sufficient to allow the sleeve covered spur to be pulled through the relatively small body incision with only said sleeve making contact with the perimeter of said incision; said sleeve being of a plastic which is sufficiently durable that it will not tear as the sleeve covered spur is drawn through the relatively small body incision; said sleeve including a notch extending axially from one end of said sleeve to a base located a sufficient distance from said one end of said sleeve to allow one to orient a clamp such that it extends laterally from said sleeve through said notch; at least one tie fixed to said sleeve in the vicinity of said one end of said sleeve for tying around the circumference of said sleeve and a colostomy spur located therein, said tie being located at a point spaced from the base of said notch toward said one end of said sleeve so that said tie overlies said notch and can be tied at a point above a clamp which is extending laterally through said notch.

11. The surgical device of claim 10 in which said sleeve includes a second tie spaced from said first tie in a direction away from said one end of said flexible sleeve a sufficient distance to allow a clamp to be located between said first and second ties when they are tied off.

12. The surgical device of claim 11 in which said second tie is located below said base of said notch, away from said one end of said sleeve.

13. The surgical device of claim 12 in which said sleeve is made of a transparent plastic material such that in use, a surgeon can observe and assess the viability of the colostomy spur located within said sleeve.

14. The surgical device of claim 13 in which the plastic of which said sleeve is made is a nylon film material.

15. The surgical device of claim 10 in which said sleeve is made of a transparent plastic material such that in use, a surgeon can observe and assess the viability of the colostomy spur located within said sleeve.

16. The surgical device of claim 10 in which the plastic of which said sleeve is made in a nylon film material.

* * * * *

UNITED STATES PATENT AND TRADEMARK OFFICE
CERTIFICATE OF CORRECTION

PATENT NO. : 4,024,872
DATED : May 24, 1977
INVENTOR(S) : James P. Muldoon

It is certified that error appears in the above–identified patent and that said Letters Patent are hereby corrected as shown below:

Column 1, line 13;
    "the" should be --The--;

Column 2, line 21;
    "viewing" should be --view--;

Column 2, line 64;
    After "flexible" insert -- plastic--;

Column 3, line 44;
    "the" should be --The--;

Column 6, line 36;
    "in" should be --is--.

Signed and Sealed this

Twenty-second Day of November 1977

[SEAL]

Attest:

RUTH C. MASON
Attesting Officer

LUTRELLE F. PARKER
Acting Commissioner of Patents and Trademarks